US006319673B1

(12) United States Patent
Beck et al.

(10) Patent No.: US 6,319,673 B1
(45) Date of Patent: Nov. 20, 2001

(54) **PCR-BASED DETECTION AND QUANTIFICATION OF *TAPESIA YALLUNDAE* AND *TAPESIA ACUFORMIS***

(75) Inventors: James Joseph Beck, Cary; Charles Jason Barnett, Chapel Hill, both of NC (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 09/635,747

(22) Filed: Aug. 10, 2000

Related U.S. Application Data

(60) Provisional application No. 60/168,326, filed on Dec. 1, 1999, and provisional application No. 60/287,548, filed on Aug. 10, 1999, now abandoned.

(51) Int. Cl.[7] .............................. C12Q 1/68; C12P 19/34; C07H 21/04

(52) U.S. Cl. ............................ 435/6; 435/91.2; 536/24.3; 536/23.1; 536/24.1

(58) Field of Search ..................... 435/6, 91.2; 536/24.3, 536/23.1, 24.1

(56) References Cited

U.S. PATENT DOCUMENTS

| | | | | |
|---|---|---|---|---|
| 5,585,238 | * | 12/1996 | Ligon et al. | 435/6 |
| 5,814,453 | * | 9/1998 | Beck | 435/6 |

OTHER PUBLICATIONS

Livak et al. PCR Methods and Applications. 4:357–362, 1995.*

Poupard et al. Plant Pathology (1993) 42, 873–881.*

* cited by examiner

*Primary Examiner*—Jeffrey Fredman
*Assistant Examiner*—Juliet Einsmann
(74) *Attorney, Agent, or Firm*—J. Timothy Meigs

(57) ABSTRACT

The present invention provides primers and probes for use in TaqMan™ quantitative PCR assays for the detection of *Tapesia yallundae* (syn. *Pseudocercosporella herpotrichoides* W-type) and *Tapesia acuformis* (syn. *Pseudocercosporella herpotrichoides* R-type). The present invention also provides primers and probes for use in TaqMan™ quantitative PCR control assays for the detection of wheat DNA.

12 Claims, No Drawings

PCR-BASED DETECTION AND QUANTIFICATION OF *TAPESIA YALLUNDAE* AND *TAPESIA ACUFORMIS*

This application claims the benefit of U.S. Provisional Application No. 60/287,548, abandoned filed Aug. 10, 1999 [Beck et al.;] and U.S. Provisional Application No. 60/168,326, filed Dec. 1, 1999. The full disclosures of both of these provisional applications are incorporated herein by reference.

FIELD OF THE INVENTION

The present invention relates to the use of primers and probes in TaqMan™ quantitative PCR assays for the detection of *Tapesia yallundae* (syn. *Pseudocercosporella herpotrichoides* W-type) and *Tapesia acuformis* (syn. *Pseudocercosporella herpotrichoides* R-type). The use of these assays enables the detection of specific fungal pathogens and their quantification in plant populations. The invention also relates to the use of primers and probes in TaqMan™ quantitative PCR assays for the detection of host wheat DNA for use as an endogenous reaction control.

BACKGROUND OF THE INVENTION

Diseases in plants cause considerable crop loss from year to year resulting both in economic deprivation to farmers and, in many parts of the world, to shortfalls in the nutritional provision for local populations. The widespread use of fungicides has provided considerable security against plant pathogen attack. However, despite $1 billion worth of expenditure on fungicides, worldwide crop losses amounted to approximately 10% of crop value in 1981 (James, 1981; *Seed Sci. & Technol.* 9: 679–685).

The severity of the destructive process of disease depends on the aggressiveness of the pathogen and the response of the host. One aim of most plant breeding programs is to increase the resistance of host plants to disease. Typically, different races of pathogens interact with different varieties of the same crop species differentially, and many sources of host resistance only protect against specific pathogen races. Furthermore, some pathogen races show early signs of disease symptoms, but cause little damage to the crop. Jones and Clifford (1983; Cereal Diseases, John Wiley) report that virulent forms of the pathogen are expected to emerge in the pathogen population in response to the introduction of resistance into host cultivars and that it is therefore necessary to monitor pathogen populations. In addition, there are several documented cases of the evolution of fungal strains that are resistant to particular fungicides. As early as 1981, Fletcher and Wolfe (1981; *Proc.* 1981 *Brit. Crop Prot. Conf.*) contended that 24% of the powdery mildew populations from spring barley and 53% from winter barley showed considerable variation in response to the fungicide triadimenol and that the distribution of these populations varied between varieties, with the most susceptible variety also giving the highest incidence of less susceptible types. Similar variation in the sensitivity of fungi to fungicides has been documented for wheat mildew (also to triadimenol), Botrytis (to benomyl), Pyrenophora (to organomercury), Pseudocercosporella (to MBC-type fungicides) and *Mycosphaerella fijiensis* to triazoles to mention just a few (Jones and Clifford; Cereal Diseases, John Wiley, 1983).

Cereal species are grown worldwide and represent a major fraction of world food production. Although yield loss is caused by many pathogens, the necrotizing pathogens Septoria and Pseudocercosporella are particularly important in the major cereal growing areas of Europe and North America (Jones and Clifford; Cereal Diseases, John Wiley, 1983). In particular, the differential symptomology caused by different isolates and species of these fungi make the accurate predictive determination of potential disease loss difficult. Consequently, the availability of improved diagnostic techniques for the rapid and accurate identification of specific pathogens will be of considerable use to field pathologists.

Eyespot of wheat is caused by the pathogens *Tapesia acuformis* and *Tapesia yallundae.* These have previously been considered varieties of the same species *Pseudocercosporella herpotrichoides* (Fron) Deighton. Wheat, rye, oats and other grasses are susceptible to the eyespot disease, which occurs in cool, moist climates and is prevalent in Europe, North and South America, Africa and Australia. Wheat is the most susceptible cereal species, but isolates have been identified that are also virulent on other cereals. The R-strain of the fungus (*Tapesia acuformis*), for example, has also been isolated from rye and grows more slowly on wheat than the W-strain (*Tapesia yallundae*) which has been isolated from wheat. Eyespot is restricted to the basal culm of the plant and can kill tillers or plants outright; however, it more usually causes lodging and/or results in a reduction in kernel size and number. Yield losses associated with eyespot are of even greater magnitude than those associated with *Septoria tritici* and *Septoria nodorum.* Typical control measures for eyespot include treatment with growth regulators to strengthen internodes, as well as fungicide treatment. However, the differing susceptibility of cultivars to different strains of the fungus render the predictive efficacy of fungicide treatments difficult.

In view of the above, there is a real need for the development of technology that will allow the identification of specific races of pathogen fungi early in the infection process. By identifying the specific race of a pathogen before disease symptoms become evident in the crop stand, the agriculturist can assess the likely effects of further development of the pathogen in the crop variety in which it has been identified and can choose an appropriate fungicide if such application is deemed necessary.

TaqMan™ chemistry and the ABI7700 (Perkin Elmer, Applied Biosystems Division, Foster City, Calif.) provide a means of creating precise, reproducible quantitative assays of DNA and RNA. The foundation of TaqMan™ chemistry is the polymerase chain reaction (PCR). In conventional PCR assays, oligonucleotide primers are designed complementary to the 5' and 3' ends of a DNA sequence of interest. During thermal cycling, DNA is first heat denatured. The sample is then brought to annealing and extension temperatures in which the primers bind their specific complements and are extended by the addition of nucleotide triphosphates by Taq polymerase. With repeated thermal cycling, the amount of template DNA is amplified.

In TaqMan™ chemistry, an oligonucleotide probe is designed that is complementary to the sequence region between the primers within the PCR amplicon. The probe contains a fluorescent reporter dye at its 5' end and a quencher dye at its 3' end. When the probe is intact, its fluorescent emissions are quenched by the phenomena of fluorescent resonance energy transfer (FRET). During thermal cycling, the probe hybridizes to the target DNA downstream of one of the primers. TaqMan™ chemistry relics on the 5' exonuclease activity of Taq polymerase to cleave the fluorescent dye from the probe. As PCR product accumulates, fluorescent signal is increased. By measuring this signal, the amplified product can be quantified. This method allows the quantitation of disease pressure by targeting pathogen DNA. In combination with the PCR primers, the probe provides another level of specificity in assays to differentiate pathogens.

SUMMARY OF THE INVENTION

The present invention is drawn to methods of identification and quantification of different species of plant pathogenic fungi. The invention provides primer and probe DNA sequences useful in TaqMan™ quantitative PCR assays. Such DNA sequences are useful in the method of the invention as they are used in polymerase chain reaction (PCR) and TaqMan™-based diagnostic assays. These primers generate unique fragments in PCR reactions in which the DNA template is provided by specific fungal pathogens. In combination with the hybridization of the TaqMan™ probe, they can be used to detect and quantify the specific pathogens in host plant material before the onset of disease symptoms.

In a preferred embodiment, the invention provides ITS-derived diagnostic primers and TaqMan™ probes for the detection of *Tapesia yallundae* (syn. *Pseudocercosporella herpotrichoides* W-type) and *Tapesia acuformis* (syn. *Pseudocercosporella herpotrichoides* R-type).

This invention provides the possibility of assessing potential damage in a specific crop variety-pathogen strain relationship and of utilizing judiciously the diverse ararmory of fungicides that is available. Furthermore, the invention can be used to provide detailed information on the development and spread of specific pathogen races over extended geographical areas. The invention provides a method of quantification of disease pressure on a given crop.

Kits useful in the practice of the invention are also provided. The kits find particular use in the identification and quantification of the fungal pathogens *Tapesia yallundae* and *Tapesia acuformis.*

BRIEF DESCRIPTION OF THE SEQUENCES IN THE SEQUENCE LISTING

SEQ ID NOs:1–34 are the following oligonucleotide probes and primers useful for PCR-based detection of the fungal pathogens *Tapesia yallundae* and *Tapesia acuformis:*

| SEQ ID NO: | Oligo | Target | Oligo Sequence (5'->3') |
|---|---|---|---|
| SEQ ID NO:1 | ITS1 | Fungal 18S rDNA | tccgtaggtgaacctgcgg |
| SEQ ID NO:2 | ITS4 | Fungal 25S rDNA | tcctccgcttattgatatgc |
| SEQ ID NO:3 | J103W | *Tapesia yallundae* (W) | ggctaccctacttggtag |
| SEQ ID NO:4 | J104W | *Tapesia yallundae* (W) | cctgggggctaccctacttg |
| SEQ ID NO:5 | J105W | *Tapesia yallundae* (W) | gggggctaccctacttggtag |
| SEQ ID NO:6 | J106W | *Tapesia yallundae* (W) | tgggggctaccctacttggtag |
| SEQ ID NO:7 | J107W | *Tapesia yallundae* (W) | (FAM)-tttagagtcgtcaggcctctcggagaagc-(TAMRA) |
| SEQ ID NO:8 | J108W | *Tapesia yallundae* (W) | atttattcaagggtggaggtcctga |
| SEQ ID NO:9 | J109W | *Tapesia yallundae* (W) | aagggtggaggtctgaaccag |
| SEQ ID NO:10 | J110W | *Tapesia yallundae* (W) | aagggtggaggtctgaacca |
| SEQ ID NO:11 | J111W | *Tapesia yallundae* (W) | caagggtggaggtctgaacc |
| SEQ ID NO:12 | J112R | *Tapesia acuformis* (R) | tcaagggtggaggtctgaacc |
| SEQ ID NO:13 | J100R | *Tapesia acuformis* (R) | gggccaccctacttcggtaa |
| SEQ ID NO:14 | J101R | *Tapesia acuformis* (R) | gaaatcctgggggccaccctacttc |
| SEQ ID NO:15 | J102R | *Tapesia acuformis* (R) | cctgggggccaccctact |
| SEQ ID NO:16 | J113R | *Tapesia acuformis* (R) | gccaccctacttcggtaaggtt |
| SEQ ID NO:17 | J114R | *Tapesia acuformis* (R) | caccctacttcggtaaggtttagagtc |
| SEQ ID NO:18 | J115R | *Tapesia acuformis* (R) | aggtaatttattcaagggtggaggt |
| SEQ ID NO:19 | J116R | *Tapesia acuformis* (R) | aggtaatttattcaagggtggaggtc |
| SEQ ID NO:20 | J117R | *Tapesia acuformis* (R) | aaggtaatttattcaagggtggaggt |
| SEQ ID NO:21 | J118R | *Tapesia acuformis* (R) | ttattcaagggtggaggtctgg |
| SEQ ID NO:22 | J119R | *Tapesia acuformis* (R) | tattcaagggtggaggtctgga |
| SEQ ID NO:23 | J120R | *Tapesia acuformis* (R) | cctgccaaagcaacaaaggta |
| SEQ ID NO:24 | J121R | *Tapesia acuformis* (R) | (FAM)-cgggcctctcggagaagcctgg-(TAMRA) |
| SEQ ID NO:25 | J122R | *Tapesia acuformis* (R) | cctacttcggtaaggtttagagtcgt |

-continued

| SEQ ID NO: | Oligo | Target | Oligo Sequence (5'->3') |
|---|---|---|---|
| SEQ ID NO:26 | J123R | *Tapesia acuformis* (R) | tctccgagaggcccgac |
| SEQ ID NO:27 | J124R | *Tapesia acuformis* (R) | (FAM)-aagcctggtccagacctccaccc-(TAMRA) |
| SEQ ID NO:28 | J125R | *Tapesia acuformis* (R) | aaggatcattaatagagcaatggatagac |
| SEQ ID NO:29 | J126R | *Tapesia acuformis* (R) | (FAM)-cgccccgggagaaatcctgg-(TAMRA) |
| SEQ ID NO:30 | J127R | *Tapesia acuformis* (R) | tgggggccaccctacttc |
| SEQ ID NO:31 | JB537 | *Tapesia yallundae* (W) | gggggctaccctacttggtag |
| SEQ ID NO:32 | JB541 | *Tapesia yallundae* (W) | ccactgattttagaggccgcgag |
| SEQ ID NO:33 | JB540 | *Tapesia acuformis* (R) | gggggccaccctacttcggtaa |
| SEQ ID NO:34 | JB542 | *Tapesia acuformis* (R) | ccactgattttagaggccgcgaa |

SEQ ID NO:35 is a forward sequencing primer.
SEQ ID NO:36 is a reverse sequencing primer.

SEQ ID NO:37 is a DNA sequence for the Internal Transcribed Spacer of *Tapesia acuformis* (syn. *P. herpotrichoides* R-type), NRRL accession no. B-21234, comprising in the 5' to 3' direction: 3' end of the small subunit rRNA gene (nucleotides 1–30), Internal Transcribed Spacer 1 (nucleotides 31–263), 5.8 S rRNA gene (nucleotides 264–419), Internal Transcribed Spacer 2 (nucleotides 420–570), and 5' end of the large subunit rRNA gene (nucleotides 571–627).

SEQ ID NO:38 is a DNA sequence for the Internal Transcribed Spacer of *Tapesia yallundae* (syn. *P. herpotrichoides* W-type), NRRL accession no. B-21231, comprising in the 5' to 3' direction: 3' end of the small subunit rRNA gene (nucleotides 1–30), Internal Transcribed Spacer 1 (nucleotides 31–262), 5.8 S rRNA gene (nucleotides 263–418), Internal Transcribed Spacer 2 (nucleotides 419–569), and 5' end of the large subunit rRNA gene (nucleotides 570–626).

SEQ ID NO:39 is a consensus DNA sequence of the partial ITS region PCR-amplified from wheat extracts from three different locations (Barton, Elmdon, Teversham) infected with *Tapesia acuformis,* comprising in the 5' to 3' direction: partial Internal Transcribed Spacer 1 sequence, 5.8 S rRNA gene, and partial Internal Transcribed Spacer 2 sequence.

SEQ ID NO:40 is a consensus DNA sequence of the partial ITS region PCR-amplified from wheat extracts from three different locations (Barton, Elmdon, Teversham) infected with *Tapesia yallundae,* comprising in the 5' to 3' direction: partial Internal Transcribed Spacer 1 sequence, 5.8 S rRNA gene, and partial Internal Transcribed Spacer 2 sequence.

SEQ ID NO:41 is the nucleotide sequence of the gene for cytochrome b-559 in wheat chloroplast DNA (Hird, et al., *Mol. Gen. Genet.* 203: 95–100 (1986)).

SEQ ID NOs:42–44 are the following oligonucleotide primers and probe useful for PCR-based detection of wheat chloroplast DNA:

| SEQ ID NO: | Oligo | Primer | Oligo Sequence (5'->3') |
|---|---|---|---|
| SEQ ID NO:42 | Forward Primer | WCP2 | cagtgcgatggctggctatt |
| SEQ ID NO:43 | Reverse Primer | WCP3 | cgttggatgaactgcattgct |
| SEQ ID NO:44 | TaqMan ™ Probe | WCP1 | (VIC)-acggactagctgtacctactgtttttttcttgggatc-(TAMRA) |

DETAILED DESCRIPTION OF THE INVENTION

The present invention provides unique DNA sequences that are useful in identifying and quantifying different pathotypes of plant pathogenic fungi. Particularly, the DNA sequences can be used as primers in TaqMan™ PCR-based analysis for the identification of fungal pathotypes. The DNA sequences of the invention include primers and probes derived from Internal Transcribed Spacer (ITS) sequences of the ribosomal RNA gene regions of particular fungal pathogens, which are capable of identifying the particular pathogen. The ITS DNA sequences from different pathotypes within a pathogen species or genus, which vary between the different members of the species or genus, can be used to identify those specific members.

Biomedical researchers have used PCR-based techniques for some time and with moderate success to detect pathogens in infected animal tissues. Only recently, however, has this technique been applied to detect plant pathogens. The presence of *Gaumannomyces graminis* in infected wheat has been detected using PCR of sequences specific to the pathogen mitochondrial genome (Schlesser et al., 1991; *Applied and Environ. Microbiol.* 57: 553–556), and random amplified polymorphic DNA (i.e. RAPD) markers were able to distinguish numerous races of *Gremmeniella abietina,* the causal agent of scleroderris canker in conifers. U.S. Pat. No. 5,585,238 (herein incorporated by reference in its entirety) describes primers derived from the ITS sequences of the ribosomal RNA gene region of strains of Septoria, Pseudocercosporella, and Mycosphaerella and their use in the identification of these fungal isolates using PCR-based techniques. In addition, WO 95/29260 (herein incorporated by reference in its entirety) describes primers derived from the ITS sequences of the ribosomal RNA gene region of strains of Fusarium and their use in the identification of these fungal isolates using PCR-based techniques. Furthermore, U.S. Pat. No. 5,800,997 (herein incorporated by reference in its entirety) describes primers derived from the ITS sequences of the ribosomal RNA gene region of strains of Cercospora, Helminthosporium, Kabatiella, and Puccinia and their use in the identification of these fungal isolates using PCR-based techniques.

Ribosomal genes are suitable for use as molecular probe targets because of their high copy number. Despite the high conservation between mature rRNA sequences, the non-transcribed and transcribed spacer sequences are usually poorly conserved and are thus suitable as target sequences for the detection of recent evolutionary divergence. Fungal rRNA genes are organized in units, each of which encodes three mature subunits of 18S (small subunit), 5.8S, and 28S (large subunit). These subunits are separated by two Internal Transcribed Spacers, ITS1 and ITS2, of around 300 bp (White et aL, 1990; In: PCR Protocols; Eds.: Innes et al.; pages 315–322). In addition, the transcriptional units are separated by non-transcribed spacer sequences (NTSs). The ITS and NTS sequences are particularly suitable for the detection of specific pathotypes of different fungal pathogens.

The DNA sequences of the invention are from the Internal Transcribed Spacer sequences of the ribosomal RNA gene region of particular plant pathogens. The ITS DNA sequences from different pathotypes within a pathogen species or genus vary among the different members of the species or genus. Once having determined the ITS sequences of a pathogen, these sequences can be aligned with other ITS sequences. In this manner, primers can be derived from the ITS sequences. That is, primers can be designed based on regions within the ITS sequences that contain the greatest differences in sequence among the fungal pathotypes. These sequences and primers based on these sequences can be used to identify specific pathogens.

Sequences of representative oligonucleotide primers derived from ITS sequences are disclosed in SEQ ID NOs:1–34. The sequences find use in TaqMan™ quantitative PCR-based identification of the pathogens of interest.

Methods for the use of the primer sequences of the invention in PCR analysis are well known in the art. For example, see U.S. Pat. Nos. 4,683,195 and 4,683,202, as well as Schlesser et al. (1991) *Applied and Environ. Microbiol.* 57:553–556. See also, Nazar et al. (1991; *Physiol. and Molec. Plant Pathol.* 39: 1–11), which used PCR amplification to exploit differences in the ITS regions of *Verticillium albo-atrum* and *Verticillium dahliae* and therefore distinguish between the two species; and Johanson and Jeger (1993; *Mycol. Res.* 97:670–674), who used similar techniques to distinguish the banana pathogens *Mycosphaerella fijiensis* and *Mycospharella musicola.*

The TaqMan™ methodology has recently been used in medical research for the quantitative detection of herpes simplex virus (HSV) DNA in clinical samples (*J. Clin. Microbial.* 37(6): 1941–7 (June, 1999)) in veterinary medicine for the detection of parasitic microbes in host animals (*J. Clin. Microbiol.* 37(5): 1329–31 (May, 1999)), and has been shown to be useful in the screening of ground beef for bacterial pathogens (*Appl. Envir. Micro.* 62(4): 1347–1353 (April, 1996)). Only recently has the TaqMan™ method been used for the identification and/or quantification of fungal pathogens in crop plants (*Phytopathology* 89(9): 796–804 (1999)).

The ITS DNA sequences of the invention can be cloned from fungal pathogens by methods known in the art. In general, the methods for the isolation of DNA from fungal isolates are known. See, Raeder & Broda (1985) *Letters in Applied Microbiology* 2:17–20; Lee et al. (1990) *Fungal Genetics Newsletter* 35:23–24; and Lee and Taylor (1990) In: *PCR Protocols: A Guide to Methods and Applications,* Innes et al. (Eds.); pages 282–287.

The ITS sequences are compared within each pathogen group to locate divergences that might be useful to test in TaqMan™ PCR assays to distinguish the different species and/or strains. From the identification of divergences, numerous primers are synthesized for each probe and tested in TaqMan™ assays. Templates used for TaqMan™ assays are firstly purified pathogen DNA, and subsequently DNA isolated from infected host plant tissue. Thus, it is possible to identify probe-primer combinations that are diagnostic, i.e. that identify one particular pathogen species or strain but not another species or strain of the same pathogen.

Preferred primer-probe combinations are able to distinguish between the different species or strains in infected host tissue, i.e. host tissue that has previously been infected with a specific pathogen species or strain. This invention provides numerous primer-probe combinations that fulfill this criterion for *Tapesia yallundae* and *Tapesia acuformis.* The primers and probes of the invention are designed based on sequence differences among the fungal ITS regions. A minimum of one base pair difference between sequences can permit design of a discriminatory primer or probe. Primer-probe combinations designed to a specific fungal pathogen's ITS region can be used in combination with a primer or probe made to a conserved sequence region within the ribosomal gene's coding region to detect amplification of species-specific PCR fragments. In general, primers should have a theoretical melting temperature ($T_M$) near 59° C. to achieve good sensitivity and should be void of significant secondary structure and 3' overlaps between primer combinations. Primer pairs' $T_M$s are typically within 2° C. of one another. Primers generally have sequence identity with at least about 5–10 contiguous nucleotide bases of ITS1 or ITS2. In preferred embodiments, primers are anywhere from approximately 5–30 nucleotide bases long. Probes are generally designed to have a $T_M$ 10° C. higher than that of the primers.

All wheat extractions contain the host wheat DNA as well as any fungal pathogen DNA present. Thus, an endogenous control assay targeting the wheat DNA can be run on extracts to account for any differences among sample extractions. The present invention describes a control assay targeting the cytochrome b-559 gene. The cytochrome b-559 gene is a conserved gene among wheat varieties, necessary for the life of the host plant. These control assays provide a control against false negatives. That is, a negative result for fungal DNA that could be attributed to inhibition of the PCR reaction is verified by an endogenous control assay. These control assays also provide a target against which the fungal DNA quantity is normalized for sample to sample comparison. The present invention describes the use of these control assays in reactions separate from the fungal pathogen assays and in multiplexed reactions. The present invention lends itself readily to the preparation of "kits" containing the elements necessary to carry out the process. Such a kit may comprise a carrier being compartmentalized to receive in close confinement therein one or more container, such as tubes or vials. One of the containers may contain unlabeled or detectably labeled DNA primers. The labeled DNA primers may be present in lyophilized form or in an appropriate buffer as necessary. One or more containers may contain one or more enzymes or reagents to be utilized in TaqMan™ PCR reactions. These enzymes may be present by themselves or in admixtures, in lyophilized form or in appropriate buffers. Finally, the kit may contain all of the additional elements necessary to carry out the technique of the invention, such as buffers, extraction reagents, enzymes, pipettes, plates, nucleic acids, nucleoside triphosphates, filter paper, and other consumables of the like.

The examples below show typical experimental protocols that can be used in the selection of suitable primer and probe sequences, the testing of primers and probes for selective and diagnostic efficacy, and the use of such primers and probes for disease and fungal isolate detection and quantification. Such examples are provided by way of illustration and not by way of limitation.

EXAMPLES

Standard recombinant DNA and molecular cloning techniques used here are well known in the art and are described by J. Sambrook, E. F. Fritsch and T. Maniatis, *Molecular Cloning: A Laboratory Manual,* Cold Spring Harbor laboratory, Cold Spring Harbor, N.Y. (1989) and by T. J. Silhavy, M. L. Berman, and L. W. Enquist, *Experiments with Gene Fusions,* Cold Spring Harbor Laboratory, Cold Spring Harbor, N.Y. (1984) and by Ausubel, F. M. et al., *Current Protocols in Molecular Biology,* pub. by Greene Publishing Assoc. and Wiley-Interscience (1987).

Example 1

Fungal Isolates and Fungal Genomic DNA Extraction

Table 1 provides a listing of the fungal test isolates used and their source. Fungi are grown in 150 ml potato dextrose broth inoculated with mycelial fragments from PDA (Potato Dextrose Agar) cultures. Cultures are incubated on an orbital shaker at 28° C. for 7–11 days. Alternatively, mycelia are isolated directly from a PDA plate. Mycelia are pelleted by centrifugation and then ground in liquid nitrogen, and total genomic DNA is extracted using the protocol of Lee and Taylor (1990; In: *PCR Protocols: A Guide to Methods and Applications;* Eds.: Innes et al.; pages 282–287).

TABLE 1

Source of Test Isolates

| Isolate | Organism | Source | Origin |
|---|---|---|---|
| 358 | *Tapesia acuformis* | Novartis[1] | — |
| 308 | *Tapesia acuformis* | Novartis[1] | — |
| 44643 | *Tapesia yallundae* | ATCC[2] | Germany |
| 44614 | *Tapesia yallundae* | ATCC[2] | Ireland |
| 60973 | *Tapesia acuformis* | ATCC[2] | Germany |
| 42040 | *Pseudocercosporella herpotrichoides* var. *herpotrichoides* | ATCC[2] | — |
| 62012 | *Pseudocercosporella aestiva* | ATCC[2] | Germany |
| 24425 | *Septoria nodorum* | ATCC[2] | Montana |
| 26517 | *Septoria tritici* | ATCC[2] | Minnesota |
| 38699 | *Septoria glycines* | ATCC[2] | Illinois |
| 22585 | *Septoria passerini* | ATCC[2] | Minnesota |
| 26380 | *Septoria avenae f. sp. triticea* | Bergstrom/Ueng[3] | Minnesota |
| 52182 | *Ceratobasidium cereale* | ATCC[2] | Ohio |
| 11404 | *Drechslera sorokiniana* | ATCC[2] | Minnesota |
| R-5391 | *Fusarium culmorum* | Nelson[4] | Germany |
| 4551 | *Fusarium moniliforme* | Novartis[1] | Indiana |
| R-8637 | *Fusarium graminearum* | Nelson[4] | Morocco |
| T-534 | *Fusarium poae* | Nelson[4] | Pennsylvania |
| 18222 | *Gerlachia nivalis* | ATCC[2] | United Kingdom |
| 093 | *Microdochium nivale* var. *majus* | Novartis[1] | — |

[1]Novartis Agribusiness Biotechnology Research, Inc., Research Triangle Park, NC, USA
[2]American Type Culture Collection, Rockville, Maryland, USA
[3]Dr. Gary Bergstrom, Cornell University, and Dr. Peter Ueng, USDA-ARS, Beltsville, Maryland.
[4]Dr. Paul Nelson, Penn State University, State College, Pennsylvania

Example 2

DNA Extraction from Wheat Stem Tissue DNA is extracted from wheat stem tissues (identified in Table 2) as follows:

(1) Up to 25 wheat samples are placed on a clean surface. A sterile scalpel is used to cut the stem just above the first tiller or root. Another cut is made 4 cm above this cut. This 4 cm section constitutes the stem tissue sample which is pooled with the additional wheat samples for bulk maceration.

(2) The stem sample is placed in a Bioreba (Reinach, Switzerland) heavy duty plastic bag (cat#490100). The plant tissue is weighed, plastic bag, with sample minus the tare (weight of the plastic bag,).

(3) An equal volume (mL) of Muller Extraction Buffer (0.1% w/v Tween-80; 0.040 M Tris base; 0.15 M Sodium chloride; 0.1% w/v Bovine serum albumin (Pentex Fraction V); 0.01% w/v Sodium azide; 0.20 M EDTA; pH to 7.7, Store at 4° C.) is added per weight (g) of wheat tissue. Tissue is macerated using a Bioreba Homex 6 homogenizer set at 70. The tissue is ground until fibrous.

(4) Extraction juice is aliquoted into eppendorf tubes on ice.

(a) Extracts are boiled for 5 minutes.

(b) Boiled extracts are kept on ice. The boiled extract is microfuged for 5 minutes at 12,000×G.

(c) 1:20 dilutions of the supernatant are made from the microfuged extract in $dH_20$.

(d) The diluted extracts are stored on ice until ready to use.

TABLE 2

Origin of Wheat Samples Used in Primer and Probe Development

| Sample | Description | Origin |
|---|---|---|
| W(Barton) | Eyespot infected wheat | United Kingdom |
| W(Elmdon) | Eyespot infected wheat | United Kingdom |
| W(Teversham) | Eyespot infected wheat | United Kingdom |
| R(Barton) | Eyespot infected wheat | United Kingdom |
| R(Elmdon) | Eyespot infected wheat | United Kingdom |
| R(Teversham) | Eyespot infected wheat | United Kingdom |

TABLE 3

Origin of Wheat Samples Used for Assay Development

| Sample | Description | Origin |
|---|---|---|
| 1999 H | Uninfected wheat | Greenhouse |
| 1999 #5 | Eyespot infected wheat | Fairfleid, WA |
| 1999 #6 | Eyespot infected wheat | Genesee, ID |
| 1999 #8 | Eyespot infected wheat | Walla Walla, WA |
| 1999 #10 | Eyespot infected wheat | Connell, WA |
| 1999 #16 | Eyespot infected wheat | Connell, WA |
| 1999 #21 | Eyespot infected wheat | Colfax, WA |
| 1999 #23 | Eyespot infected wheat | Colfax, WA |
| 1999 #33 | Eyespot infected wheat | Athena, OR |
| 1999 #38 | Eyespot infected wheat | Leland, ID |
| 1999 #41 | Eyespot infected wheat | Coulee City, WA |
| 1999 #43 | Eyespot infected wheat | Genesee, ID |
| 1999 #46 | Eyespot infected wheat | Leland, ID |
| 1999 #47 | Eyespot infected wheat | Leland, ID |
| 1999 #54 | Eyespot infected wheat | Wilur, WA |
| 1999 #56 | Eyespot infected wheat | Ritzville, WA |
| 1999 #57 | Eyespot infected wheat | Sprague, WA |
| 1999 #72 | Eyespot infected wheat | Grangeville, IO |
| 1999 #73 | Eyespot infected wheat | Grangeville, IO |
| 1999 #74 | Eyespot infected wbeat | Grangeville, IO |
| 1999 #80 | Eyespot infected wheat | Ritzville, WA |
| 1999 #82 | Eyespot infected wheat | Edwall, WA |
| 1999 #84 | Eyespot infected wheat | Genesee, ID |
| 1999 #93 | Eyespot infected wheat | Davenport, WA |
| 1999 #88 | Eyespot infected wheat | Wilbur, WA |
| 1999 #89 | Eyespot infected wheat | Coulee City, WA |
| 1999 #94 | Eyespot infected wheat | Plummee, ID |
| 1999 #95 | Eyespot infected wheat | Pendleton, OR |
| 1999 #96 | Eyespot infected wheat | Harrington, WA |
| 1999 #100 | Eyespot infected wheat | Creston, WA |
| 1999 #108 | Eyespot infected wheat | Wilbur, WA |
| 1999 #111 | Eyespot infected wheat | Ferdinand, ID |

Example 3

Isolation and Sequencing of the Internal Transcribed Spacer (ITS) Region DNA from *Tapesia yallundae* and *Tapesia acuformis* Infected Wheat Samples Approximately 420-bp truncated ITS region fragments are PCR-amplified from wheat extracts identified in Table 2 infected with *Tapesia yallundae* using the *Tapesia yalludae*-specific primers JB537 (SEQ ID NO:31) and JB541 (SEQ ID NO:32). Similarly, the *Tapesia acuformis* truncated ITS fragments are amplified from *Tapesia acuformis*-infected wheat extracts using *Tapesia acuformis*-specific primers JB540 (SEQ ID NO:33) and JB542 (SEQ ID NO:34). Polymerase chain reactions are performed with the Gene-Amp Kit from Perkin-Elmer (Foster City, Calif.; part no. N808-0009) using 50 mM KCl, 2.5 mM $MgCl_2$, 10 mM Tris-HCl, pH 8.3, containing 200 $\mu$M of each dTTP, dATP, dCTP, and dGTP, 50 pmol each primer, 2.5 units of Taq polymerase and 1 $\mu$l 1:10 diluted wheat extract in a final volume of 50 $\mu$l. Reactions are run at 94° C. for 15 s and 1 min. at 75° C. for 35 cycles in a Perkin-Elmer Model 9700 thermal cycler.

The PCR products are cloned into the pCR®2.1-TOPO TA-cloning vector using the TOPO-TA Cloning Kit (Invitrogen, Carlsbad, Calif.; part no. K4550-40) according to manufacturer's directions. Clones containing the ITS fragment inserts are sequenced using the TA cloning vector's FORWARD (5'-gtaaaacgacggccagt-3'; SEQ ID NO:35) and REVERSE (5'-caggaaacagctatgac-3'; SEQ ID NO:36) primers. Sequencing is performed on an ABI PRISM 377™ DNA sequencer (Perkin Elmer Applied Biosystems, Foster City, Calif.).

Example 4

Synthesis and Purification of Oligonucleotides

Oligonucleotides and TaqMan™ probes (primers and probes) are synthesized and purified by, for example, either Integrated DNA Technologies (Coralville, Iowa) or Midland Certified Reagent Company (Midland, Tex.).

Example 5

Selection of Species-Specific Primers and Probes

A multiple sequence alignment is made of ITS region consensus sequences of *Tapesia yallundae* (SEQ ID NO:40) and *Tapesia acuformis* (SEQ ID NO:39) obtained from infected wheat tissue as described in Example 3. Also included in the alignment are ITS region sequences from *Tapesia yallundae* and *Tapesia acuformis* fungal DNAs referenced in U.S. Pat. No. 5,585,238 (SEQ ID NO:37 and SEQ ID NO:38, respectively). PCR primers and TaqMan™ probes are designed to the regions that contain the greatest differences in sequence between the fungal species. This produces primers and probes designed to be specific to either *Tapesia acuformis* or *Tapesia yallundae*. The oligonucleotide primers and probes shown below in Tables 4 and 5 are synthesized according to Example 4. The previously described (U.S. Pat. No. 5,585,238) *Tapesia yallundae*-specific primers JB537 (SEQ ID NO:31) and JB541 (SEQ ID NO:32), and *Tapesia acuformis*-specific primers JB540 (SEQ ID NO:33) and JB542 (SEQ ID NO:34) are also synthesized. In addition, the ribosomal gene-specific primers ITS1 (SEQ ID NO:1) and ITS4 (SEQ ID NO:2) published by White et al. (1990: In: PCR Protocols; Eds.: Innes et al. Pages 315–322) are synthesized for testing in combination with the primers specific for the ITS regions.

TABLE 4

Primers and Probes for TaqMan ™ Amplification of *Tapesia acuformis* DNA

| SEQ ID NO: | Oligo | Target | Oligo Sequence (5'->3') |
|---|---|---|---|
| SEQ ID NO:1 | ITS1 | Fungal 18S rDNA | tccgtaggtgaacctgcgg |
| SEQ ID NO:2 | ITS4 | Fungal 25S rDNA | tcctccgcttattgatatgc |
| SEQ ID NO:12 | J112R | *Tapesia acuformis* (R) | tcaagggtggaggtctgaacc |
| SEQ ID NO:13 | J100R | *Tapesia acuformis* (R) | gggccaccctacttcggtaa |
| SEQ ID NO:14 | J101R | *Tapesia acuformis* (R) | gaaatcctgggggccaccctacttc |
| SEQ ID NO:15 | J102R | *Tapesia acuformis* (R) | cctgggggccaccctact |
| SEQ ID NO:16 | J113R | *Tapesia acuformis* (R) | gccaccctacttcggtaaggtt |
| SEQ ID NO:17 | J114R | *Tapesia acuformis* (R) | caccctacttcggtaaggtttagagtc |
| SEQ ID NO:18 | J115R | *Tapesia acuformis* (R) | aggtaatttattcaagggtggaggt |
| SEQ ID NO:19 | J116R | *Tapesia acuformis* (R) | aggtaatttattcaagggtggaggtc |
| SEQ ID NO:20 | J117R | *Tapesia acuformis* (R) | aaggtaatttattcaagggtggaggt |
| SEQ ID NO:21 | J118R | *Tapesia acuformis* (R) | ttattcaagggtggaggtctgg |
| SEQ ID NO:22 | J119R | *Tapesia acuformis* (R) | tattcaagggtggaggtctgga |

TABLE 4-continued

Primers and Probes for TaqMan ™ Amplification of *Tapesia acuformis* DNA

| SEQ ID NO: | Oligo | Target | Oligo Sequence (5'->3') |
|---|---|---|---|
| SEQ ID NO:23 | J120R | *Tapesia acuformis* (R) | cctgccaaagcaacaaaggta |
| SEQ ID NO:24 | J121R | *Tapesia acuformis* (R) | (FAM)-cgggcctctcggagaagcctgg-(TAMRA) |
| SEQ ID NO:25 | J122R | *Tapesia acuformis* (R) | cctacttcggtaaggtttagagtcgt |
| SEQ ID NO:26 | J123R | *Tapesia acuformis* (R) | tctccgagaggcccgac |
| SEQ ID NO:27 | J124R | *Tapesia acuformis* (R) | (FAM)-aagcctggtccagacctccaccc-(TAMRA) |
| SEQ ID NO:28 | J125R | *Tapesia acuformis* (R) | aaggatcattaatagagcaatggatagac |
| SEQ ID NO:29 | J126R | *Tapesia acuformis* (R) | (FAM)-cgccccgggagaaatcctgg-(TAMRA) |
| SEQ ID NO:30 | J127R | *Tapesia acuformis* (R) | tgggggccaccctacttc |
| SEQ ID NO:33 | JB540 | *Tapesia acuformis* (R) | gggggccaccctacttcggtaa |
| SEQ ID NO:34 | JB542 | *Tapesia acuformis* (R) | ccactgattttagaggccgcgaa |

TABLE 5

Primers and Probes for TaqMan ™ Amplification of *Tapesia yallundae* DNA

| SEQ ID NO: | Primer | Target | Oligo Sequence (5'->3') |
|---|---|---|---|
| SEQ ID NO:1 | ITS1 | Fungal 18S rDNA | tccgtaggtgaacctgcgg |
| SEQ ID NO:2 | ITS4 | Fungal 25S rDNA | tcctccgcttattgatatgc |
| SEQ ID NO:3 | J103W | *Tapesia yallundae* (W) | ggctaccctacttggtag |
| SEQ ID NO:4 | J104W | *Tapesia yallundae* (W) | cctgggggctaccctacttg |
| SEQ ID NO:5 | J105W | *Tapesia yallundae* (W) | gggggctaccctacttggtag |
| SEQ ID NO:6 | J106W | *Tapesia yallundae* (W) | tgggggctaccctacttggtag |
| SEQ ID NO:7 | J107W | *Tapesia yallundae* (W) | (FAM)-tttagagtcgtcaggcctctcggagaagc-(TAMRA) |
| SEQ ID NO:8 | J108W | *Tapesia yallundae* (W) | atttattcaagggtggaggtcctga |
| SEQ ID NO:9 | J109W | *Tapesia yallundae* (W) | aagggtggaggtctgaaccag |
| SEQ ID NO:10 | J110W | *Tapesia yallundae* (W) | aagggtggaggtctgaacca |
| SEQ ID NO:11 | J111W | *Tapesia yallundae* (W) | caagggtggaggtctgaacc |
| SEQ ID NO:31 | JB537 | *Tapesia yallundae* (W) | gggggctaccctacttggtag |
| SEQ ID NO:32 | JB541 | *Tapesia yallundae* (W) | ccactgattttagaggccgcgag |

Example 6

Initial Screening of the Primer-Probe Library

The species-specific primer libraries designed in Example 5 are tested in initial TaqMan™ screens. Primer and probe combinations are tested for their ability to amplify from the target pathogen's DNA. All other reaction conditions are held constant (1× TaqMan™ Universal Master Mix (Perkin Elmer, Norwalk, Conn.; part no. N430-4447), 200 nM each primer, 100 nM probe, 0.04 ng/μL fungal target genomic DNA, thermal cycling: 50° C. for 2 min., 95° C. for 10 min., 40 cycles of 95° C. for 15 s, 60° C. for 60 s). Pathogen-specific primers and probes are determined by identifying those that best amplify the targeted DNA.

Example 7

TaqMan™ Primer Optimization

Once a primer pair specific for the targeted pathogen's DNA has been identified, the primer concentrations are optimized in a single TaqMan™ run. A matrix of different concentrations of the forward primer are run against those of the reverse primer with all other reaction conditions held constant (1× TaqMan™ Universal Master Mix (Perkin Elmer), 100 nM probe, 0.4 ng/μL fungal target genomic DNA, thermal cycling: 50° C. for 2 min., 95° C. for 10 min., 40 cycles of 95° C. for 15 s, 60° C. for 60 s).

Example 8

TaqMan™ Probe Optimization

Once optimal primer concentrations are determined as in Example 7, the probe concentration is optimized. With primers at their optimal concentrations, different concentrations of probe are run in a typical TaqMan™ run. The probe concentration that gives the best signal in reporting the PCR amplification is chosen. The optimal primers and probe for quantification of *Tapesia acuformis* and *Tapesia yallundae* are recorded along with their optimal reaction concentrations (Tables 6 and 7, respectively). The *T. acuformis* and *T. yallundae* assays are established with an annealing temperature of 60° C. over 35 cycles.

TABLE 6

Primer and Probe Combinations Specific for *Tapesia acuformis.*

| Target | Oligo | Sequence Identifier | Primer Name | Optimized Concentration (nM) |
|---|---|---|---|---|
| *Tapesia acuformis* (R) | Forward Primer | SEQ ID NO: 14 | J101R | 50 |
| | Reverse Primer | SEQ ID NO: 18 | J115R | 900 |
| | TaqMan ™ Probe | SEQ ID NO: 24 | J121R | 700 |

TABLE 7

Primer and Probe Combinations Specific for *Tapesia yallundae.*

| Target | Oligo | Sequence Identifier | Primer Name | Optimized Concentration (nM) |
|---|---|---|---|---|
| *Tapesia yallundae* (W) | Forward Primer | SEQ ID NO: 3 | J103W | 300 |
| | Reverse Primer | SEQ ID NO: 8 | J108W | 300 |
| | TaqMan ™ Probe | SEQ ID NO: 7 | J107W | 200 |

Example 9

Determination of TaqMan™ Assay Specificity to Fungal Genomic DNA

The TaqMan™ assay is validated against a panel of DNA from other cereal pathogens for cross-reactivity (Table 1). TaqMan™ reactions are prepared using the optimal primer and probe concentrations as determined in Examples 7 and 8 and tested against 0.2 ng/μL of the genomic DNA from the cereal pathogens as prepared in Example 1. Depending on the results, changes are made to the thermal cycling parameters to make the assay more stringent. These include changing the annealing/extension temperature or the number of cycles in the run. A successful TaqMan™ assay is sensitive to sub-picogram amounts of target DNA without any cross-reactivity to the panel of cereal pathogens or the plant DNA. In Table 8 results of the *Tapesia acuformis* (R-type) and *Tapesia yallundae* (W-type) assays documented under Example 8 are shown. $C_T$ values are used to show amplification among isolates screened. Those isolates with a $C_T$ value of 35 give no amplification with the assays.

TABLE 8

Results of *Tapesia acuformis* TaqMan ™ Assay on Fungal Genomic DNA Samples

| Isolate | Organism | $C_T$ Value R-type assay | $C_T$ Value W-type assay |
|---|---|---|---|
| 358 | *Tapesia acuformis* | 18.52 | 35 |
| 308 | *Tapesia acuformis* | 18.65 | 35 |
| 44643 | *Tapesia yallundae* | 35 | |
| 44614 | *Tapesia yallundae* | 35 | 17.18 |
| 60973 | *Tapesia acuformis* | 31.36 | 35 |
| 42040 | *Pseudocercosporella herpotrichoides* var. *herpotrichoides* | 35 | 18.7 |
| 62012 | *Pseudocercosporella aestiva* | 35 | 35 |
| 24425 | *Septoria nodorum* | 35 | 35 |
| 26517 | *Septoria tritici* | 35 | 35 |
| 38699 | *Septoria glycines* | 35 | 35 |
| 22585 | *Septoria passerini* | 35 | 35 |
| 26380 | *Septoria avenae f. sp. triticea* | 35 | 35 |
| 52182 | *Ceratobasidium cereale* | 35 | 35 |
| 11404 | *Drechslera sorokiniana* | 35 | 35 |
| R-5391 | *Fusarium culmorum* | 35 | 35 |
| 4551 | *Fusarium moniliforme* | 35 | 35 |
| R-8637 | *Fusarium graminearum* | 35 | 35 |
| T-534 | *Fusarium poae* | 35 | 35 |
| 18222 | *Gerlachia nivalis* | 35 | 35 |
| 093 | *Microdochium nivale* var. *majus* | 35 | 35 |

Note:
$C_T$ value or threshold cycle, represents the PCR cycle at which an increase in reporter fluorescence above a baseline signal can first be detected.
The Sequence Detection software generates a Standard Curve of $C_T$ vs. (LogN) Starting Copy Number for all standards and then determines the starting copy number of unknowns by interpolation.

Example 10

Determination of TaqMan™ Assay Specificity to Pathogen in Infected Wheat

Wheat samples are identified as *Tapesia acuformis* and/or *Tapesia yallundae* infected based on analysis using the assays described in Example 3. Wheat samples are also tested using the primer combinations listed in Table 6 and the PCR conditions in Example 8. Using Sequence Detection Systems software (Perkin Elmer-Applied Biosciences), the amplification of pathogen DNA from the wheat samples is quantified against a standard curve of the fungal target's genomic DNA (Table 9). Results for the *Tapesia acuformis* specific assay are presented in Table 10. DNA from *Tapesia acuformis* is detected and quantified in all infected samples. Results for the *Tapesia yallundae* specific assay are presented in Table 11. DNA from *Tapesia yallundae* is detected and quantified in all infected samples. No cross-reactivity is observed in uninfected wheat tissue for either assay.

TABLE 9

Standard Curve of *Tapesia acuformis* and *T. yallundae* Genomic DNAs Run in Duplicate Against the R-type and W-type Assays, Respectively.

| R-type Assay | | W-type Assay | |
|---|---|---|---|
| *Tapesia acuformis* #308 DNA | $C_T$ Value | *Tapesia yallundae* #42040 DNA | $C_T$ Value |
| 5 ng | 18.57 | 5 ng | 18.13 |
| | 18.38 | | 17.92 |
| 500 pg | 21.3 | 500 pg | 21.83 |
| | 21.35 | | 22.02 |
| 50 pg | 23.57 | 50 pg | 25.26 |
| | 24.27 | | 25.37 |
| 5 pg | 27.82 | 5 pg | 29.53 |
| | 27.89 | | 29.88 |
| 500 fg | 31.47 | 500 fg | 33.32 |
| | 31.17 | | 35 |
| 50 fg | 34.13 | No Template Control | 35 |
| | 34.01 | | 35 |
| No Template Control | 35 | | |
| | 35 | | |

TABLE 10

Results of the *Tapesia acuformis* TaqMan ™ Assay on Wheat Extractions. Samples Are Run in Duplicate and are Documented with Results of Conventional PCR Assays

| | TaqMan ™ Results for *Tapesia acuformis* assay | | | | PCR Testing Results (0 to +5 scale) | |
|---|---|---|---|---|---|---|
| Sample Number | Cτ Value | Template (pg) | Standard Deviation | Mean (pg) | *T. acuformis* | *T. yallundae* |
| H | 35 | 0 | 0 | 0 | – | – |
| | 35 | 0 | 0 | 0 | | |
| 6 | 35 | 2.50E–02 | 0 | 0.02 | – | – |
| | 35 | 2.50E–02 | 0 | 0.02 | | |

TABLE 10-continued

Results of the *Tapesia acuformis* TaqMan ™ Assay on Wheat Extractions. Samples Are Run in Duplicate and are Documented with Results of Conventional PCR Assays

| | TaqMan ™ Results for *Tapesia acuformis* assay | | | | PCR Testing Results (0 to +5 scale) | |
|---|---|---|---|---|---|---|
| Sample Number | Cт Value | Template (pg) | Standard Deviation | Mean (pg) | *T. acuformis* | *T. yallundae* |
| 57 | 31.07 | 4.60E−01 | 0.03 | 0.44 | + | − |
| | 31.20 | 4.20E−01 | 0.03 | 0.44 | | |
| 47 | 31.13 | 4.40E−01 | 0.14 | 0.54 | + | − |
| | 30.62 | 6.40E−01 | 0.14 | 0.54 | | |
| 84 | 33.68 | 7.00E−02 | 0.01 | 0.06 | + | − |
| | 33.96 | 5.70E−02 | 0.01 | 0.06 | | |
| 23 | 29.42 | 1.50E+00 | 0.28 | 1.71 | ++ | − |
| | 29.10 | 1.90E+00 | 0.28 | 1.71 | | |
| 46 | 28.67 | 2.60E+00 | 0.44 | 2.90 | ++ | − |
| | 28.37 | 3.20E+00 | 0.44 | 2.90 | | |
| 73 | 30.54 | 6.70E−01 | 0.06 | 0.72 | ++ | − |
| | 30.37 | 7.60E−01 | 0.06 | 0.72 | | |
| 21 | 27.34 | 6.80E+00 | 2.28 | 5.15 | +++ | − |
| | 28.24 | 3.50E+00 | 2.28 | 5.15 | | |
| 38 | 30.04 | 9.70E−01 | 0.71 | 1.47 | +++ | − |
| | 29.05 | 2.00E+00 | 0.71 | 1.47 | | |
| 43 | 26.12 | 1.60E+01 | 0.97 | 16.94 | +++ | − |
| | 26.01 | 1.80E+01 | 0.97 | 16.94 | | |
| 41 | 24.07 | 7.20E+01 | 19.75 | 57.57 | ++++ | − |
| | 24.75 | 4.40E+01 | 19.75 | 57.57 | | |
| 72 | 28.01 | 4.20E+00 | 0.29 | 3.96 | ++++ | − |
| | 28.16 | 3.80E+00 | 0.29 | 3.96 | | |
| 74 | 26.01 | 1.80E+01 | 3.03 | 19.75 | ++++ | − |
| | 25.71 | 2.20E+01 | 3.03 | 19.75 | | |
| 5 | 26.72 | 1.10E+01 | 1.50 | 9.51 | +++++ | − |
| | 27.03 | 8.50E+00 | 1.50 | 9.51 | | |
| 82 | 26.74 | 1.00E+01 | 1.29 | 9.51 | +++++ | − |
| | 27.01 | 8.60E+00 | 1.29 | 9.51 | | |
| 93 | 26.05 | 1.70E+01 | 2.12 | 18.68 | +++++ | + |
| | 25.82 | 2.00E+01 | 2.12 | 18.68 | | |
| 96 | 24.07 | 7.10E+01 | 3.75 | 68.50 | +++++ | ++ |
| | 24.18 | 6.60E+01 | 3.75 | 68.50 | | |

TABLE 11

Results of the *Tapesia yallundae* TaqMan ™ Assay on Wheat Extractions. Samples Are Run in Duplicate and are Documented with Results of Conventional PCR Assays

| | TaqMan ™ Results for *Tapesia acuformis* assay | | | | PCR Testing Results (0 to +5 scale) | |
|---|---|---|---|---|---|---|
| Sample Number | Cт Value | Template (pg) | Standard Deviation | Mean (pg) | *T. acuformis* | *T. yallundae* |
| H | 35 | 0 | 0 | 0 | − | − |
| | 35 | 0 | 0 | 0 | | |
| 6 | 35 | 0 | 0 | 0 | − | − |
| | 35 | 0 | 0 | 0 | | |
| 82 | 33.41 | 4.5E−01 | 0.07 | 0.40 | +++++ | − |
| | 33.78 | 3.6E−01 | | | | |
| 94 | 33.29 | 5.2E−01 | 0.21 | 0.37 | + | + |
| | 34.68 | 2.2E−01 | | | | |
| 108 | 34.41 | 2.6E−01 | 0 | 0.26 | +++ | + |
| | 34.40 | 2.7E−01 | | | | |
| 111 | 33.21 | 5.4E−01 | 0.02 | 0.53 | ++ | + |
| | 33.28 | 5.2E−01 | | | | |
| 33 | 24.67 | 9.1E+01 | 37.45 | 64.30 | ++ | ++ |
| | 26.13 | 3.8E+01 | | | | |
| 54 | 28.09 | 1.2E+01 | 6.31 | 16.10 | +++ | ++ |
| | 27.14 | 2.1E+01 | | | | |
| 80 | 26.43 | 3.1E+01 | 3.62 | 34.03 | ++++ | ++ |
| | 26.18 | 3.7E+01 | | | | |
| 95 | 29.98 | 3.8E+00 | 0.08 | 3.7 | − | ++ |
| | 30.03 | 3.6E+00 | | | | |

TABLE 11-continued

Results of the *Tapesia yallundae* TaqMan ™ Assay on Wheat Extractions. Samples Are Run in Duplicate and are Documented with Results of Conventional PCR Assays

| | TaqMan ™ Results for *Tapesia acuformis* assay | | | | PCR Testing Results (0 to +5 scale) | |
|---|---|---|---|---|---|---|
| Sample Number | CT Value | Template (pg) | Standard Deviation | Mean (pg) | *T. acuformis* | *T. yallundae* |
| 100 | 27.16 | 2.0E+01 | 1.40 | 21.32 | +++ | +++ |
| | 27.01 | 2.2E+01 | | | | |
| 8 | 25.63 | 5.1E+01 | 9.96 | 57.91 | + | +++ |
| | 25.22 | 6.5E+01 | | | | |
| 10 | 22.36 | 3.6E+02 | 79.1 | 418.46 | ++ | +++ |
| | 21.91 | 4.7E+02 | | | | |
| 16 | 23.77 | 1.6E+02 | 6.18 | 150.78 | ++ | ++++ |
| | 23.87 | 1.5E+02 | | | | |
| 56 | 25.14 | 6.8E+01 | 2.26 | 66.56 | ++++ | ++++ |
| | 25.22 | 6.5E+01 | | | | |
| 88 | 24.48 | 1.0E+02 | 21.89 | 85.90 | ++ | ++++ |
| | 25.09 | 7.0E+01 | | | | |
| 89 | 23.87 | 1.5E+02 | 16.48 | 157.85 | ++++ | +++++ |
| | 23.63 | 1.7E+02 | | | | |

Example 11

An Endogenous Control to be Used with the Fungal Pathogen TaqMan™ Assays

All wheat extractions contain the host wheat DNA as well as any fungal pathogen DNA present. Thus, an endogenous control assay targeting the wheat DNA is run on extracts to account for any differences among sample extractions. These assays provide a control against false negatives. That is, a negative result for fungal DNA that could be attributed to inhibition of the PCR reaction is verified by this endogenous control assay. These assays also provide a target against which the fungal DNA quantity is normalized for sample to sample comparison.

Example 12

Selection of Endogenous Control Primers and Probes

Primers and probes for the amplification and detection of wheat chloroplast DNA are drawn to the coding sequence of the cytochrome b-599 gene (SEQ ID NO:41). Selection of primer and probe sequences is performed using the ABI Primer Express program (PE Applied Biosystems, Foster City, Calif., USA) according to manufacturer's instructions. This program selects TaqMan™ primer and probe sets optimized by melting temperature, secondary structure, base composition, and amplicon length. From the sets chosen by the software, a best set is selected by manually finding primers with the fewest number of thermodynamically stable bases at the 3' end. The primer/probe set chosen for the amplification of wheat DNA as an endogenous control is documented in Table 12. These are synthesized as in Example 4.

Example 13

Use of a TaqMan™ Assay to Quantify Wheat DNA in Wheat Extractions

Extractions of wheat tissue are made as in Example 2. The assay presented in Example 11 is run against these tissues as follows: Reactions are prepared in thin-walled optical grade PCR tubes (PE Applied Biosystems, Foster City, Calif., USA). Reaction mixtures are made by bringing forward and reverse primer concentrations to 900 nM and probe concentration to 250 nM in a 1× solution of TaqMan™ Universal Master Mix (PE Applied Biosystems, Foster City, Calif., USA). One microliter of 1:20 diluted wheat extract is added. Additionally, cross-reactivity with fungal DNA is tested by adding 1 μL of 5 ng/μL fungal DNA preparation. The reactions are carried out in a ABI 7700 instrument (PE Applied Biosystems, Foster City, Calif., USA), thermal cycling: 50° C. for 2 min., 95° C. for 10 min., 40 cycles of 95° C. for 15 s, 60° C. for 60 s). The ABI 7700 software determines the CT value at which the fluoresence of each reaction reaches a threshold value of 0.4. This data is presented in Table 13. The CT values presented correspond inversely with the amount of wheat target DNA present in each sample. Samples in which a CT of 40 are reported show no amplification. Table 13 shows that the endogenous control assay detects the cytochrome b-559 gene in multiple varieties of wheat. The TaqMan™ assay for wheat chloroplast DNA also shows that different amounts of host DNA are present in each sample. By using dilutions of target DNA, a standard curve can be generated as described in Example 10 against which the wheat DNA can be quantified.

TABLE 12

Primer And Probe Combinations For An Endogenous Control Reaction Targeting Wheat (*Triticum aestivum*) Chloroplast DNA.

| Oligo | SEQ ID NO: | Primer | Oligo Sequence (5'->3') |
|---|---|---|---|
| Forward Primer | SEQ ID NO:42 | WCP2 | cagtgcgatggctggctatt |
| Reverse Primer | SEQ ID NO:43 | WCP3 | cgffggatgaactgcattgct |
| TaqManTM Probe | SEQ ID NO:44 | WCP1 | (VIC)-acggactagctgtacctactgtttttttcttgggatc-(TAMRA) |

TABLE 13

CT Values Reported For A TaqMan ™ Assay Targeting Wheat Chloroplast DNA In Wheat And Fungal DNA Extractions.

| Sample Number | Wheat Variety | CT Value |
|---|---|---|
| 6 | Madsen | 17.17 |
| 57 | Madsen | 19.48 |
| 73 | Lambert | 20.71 |
| 21 | Brundage | 18.9 |
| 41 | Eltan | 20.23 |
| 13 | Mixed | 19.99 |
| 5 | Madsen | 19.19 |
| 5 ng *Tapesia acuformis* DNA #308 | | 40 |
| NTC | | 40 |

Example 14

Multiplexing of TaqMan™ Assays for Fungal Pathogens and Control Assay for Host DNA The reaction presented in Example 13 is multiplexed with reactions for quantification of fungal DNA such that both tests take place in the same reaction tube. The probe and primers for *Tapesia acuformis* documented in Table 6 at their optimized concentrations are added to the reactions described in Example 13. These reactions are run as described on infected wheat tissue. The data presented here show that TaqMan™ fungal pathogen assays may be run in the same reaction tube as an endogenous control reaction for the wheat tissue.

TABLE 14

Cт Values Reported For A TaqMan ™ Assay Targeting Wheat Chloroplast DNA In Wheat DNA Extractions.

| | | R-type Assay | | PCR Testing Results (0 to +5 scale) | |
|---|---|---|---|---|---|
| Sample Number | Wheat assay Cт Value | Cт Value | Calculated Concentration (pg) | *T. acuformis* | *T. yallundae* |
| 6 | 17.09 | 40 | 0 | – | – |
| 41 | 27.70 | 20.65 | 24.3 | ++++ | – |
| 13 | 30.9 | 19.99 | 3.69 | +++++ | + |

While the present invention has been described with reference to specific embodiments thereof, it will be appreciated that numerous variations, modifications, and further embodiments are possible, and accordingly, all such variations, modifications and embodiments are to be regarded as being within the scope of the present invention.

What is claimed is:

1. An oligonucleotide primer selected from the group consisting of SEQ ID NOs:3, 4, 8, 9, 10, 11, 12, 14, and 18.

2. A pair of oligonucleotide primers, wherein at least one of said primers is the oligonucleotide primer of claim 1.

3. A pair of oligonucleotide primers according to claim 2, wherein said pair consists of SEQ ID NO:14 and SEQ ID NO:18.

4. A pair of oligonucleotide primers according to claim 2, wherein said pair consists of SEQ ID NO:3 and SEQ ID NO:8.

5. A method for the detection of a fungal pathogen, comprising:

(a) isolating DNA from a plant leaf infected with a pathogen;

(b) subjecting said DNA to polymerase chain reaction amplification using at least one primer according to claim 1; and (c) detecting said fungal pathogen by visualizing the product or products of said polymerase chain reaction amplification.

6. The method of claim 5, wherein said fungal pathogen is *Tapesia yallundae* or *Tapesia acuformis.*

7. A method for the detection of a fungal pathogen, comprising:

(a) isolating DNA from plant tissue infected with said fungal pathogen;

(b) amplifying a part of the Internal Transcribed Spacer sequence of said fungal pathogen using said DNA as a template in a polymerase chain reaction with a pair of primers according to claim 2; and (c) detecting said fungal pathogen by visualizing the amplified part of the Internal Transcribed Spacer sequence.

8. The method of claim 7, wherein said fungal pathogen is *Tapesia yallundae* or *Tapesia acuformis.*

9. A diagnostic kit used in detecting a fungal pathogen, comprising the primer of claim 1.

10. A diagnostic kit used in detecting a fungal pathogen, comprising the pair of primers of claim 2.

11. An oligonucleotide primer pair/probe set for quantifying fungal DNA, wherein said primer pair consists of the pair of primers according to claim 3 and the probe is SEQ ID NO:24.

12. An oligonucleotide primer pair/probe set for quantifying fungal DNA, wherein said primer pair consists of the pair of primers according to claim 4 and the probe is SEQ ID NO:7.

* * * * *

SEQUENCE LISTING

```
<160> NUMBER OF SEQ ID NOS:  44

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence:ITS1

<400> SEQUENCE: 1

tccgtaggtg aacctgcgg                                          19


<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:ITS2

<400> SEQUENCE: 2

tcctccgctt attgatatgc                                         20


<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence:J103W

<400> SEQUENCE: 3

ggctacccta cttggtag                                           18


<210> SEQ ID NO 4
<211> LENGTH: 20
<212> TYPE: DNA
```

-continued

```
<213> ORGANISM: Artificial Sequence
<220> FEATURE:
<223> OTHER INFORMATION: Description of Artificial Sequence:J104W

<400> SEQUENCE: 4

cctgggggct accctacttg                                                  20


<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence:J105W

<400> SEQUENCE: 5

gggggctacc ctacttggta g                                                21


<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence:J106W

<400> SEQUENCE: 6

tgggggctac cctacttggt ag                                               22


<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence:J107W

<400> SEQUENCE: 7

tttagagtcg tcaggcctct cggagaagc                                        29


<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence:J108W

<400> SEQUENCE: 8

atttattcaa gggtggaggt cctga                                            25


<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:J109W

<400> SEQUENCE: 9

aagggtggag gtctgaacca g                                                21


<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:J110W

<400> SEQUENCE: 10

aagggtggag gtctgaacca                                                  20
```

-continued

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:J111W

<400> SEQUENCE: 11
caagggtgga ggtctgaacc 20

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence:J112R

<400> SEQUENCE: 12
tcaagggtgg aggtctgaac c 21

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:J100R

<400> SEQUENCE: 13
gggccaccct acttcggtaa 20

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence:J101R

<400> SEQUENCE: 14
gaaatcctgg gggccaccct acttc 25

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence:J102R

<400> SEQUENCE: 15
cctgggggcc accctact 18

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence:J113R

<400> SEQUENCE: 16
gccaccctac ttcggtaagg tt 22

<210> SEQ ID NO 17
<211> LENGTH: 27
<212> TYPE: DNA
<213> ORGANISM: Artificial Sequence
<220> FEATURE:

-continued

<223> OTHER INFORMATION: Description of Artificial Sequence:J114R

<400> SEQUENCE: 17
caccctactt cggtaaggtt tagagtc 27

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence:J115R

<400> SEQUENCE: 18
aggtaattta ttcaagggtg gaggt 25

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence:J116R

<400> SEQUENCE: 19
aggtaattta ttcaagggtg gaggtc 26

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence:J117R

<400> SEQUENCE: 20
aaggtaattt attcaagggt ggaggt 26

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence:J118R

<400> SEQUENCE: 21
ttattcaagg gtggaggtct gg 22

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence:J119r

<400> SEQUENCE: 22
tattcaaggg tggaggtctg ga 22

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence:J120R

<400> SEQUENCE: 23
cctgccaaag caacaaaggt a 21

-continued

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence:J121R

<400> SEQUENCE: 24
cgggcctctc ggagaagcct gg 22

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence:J122R

<400> SEQUENCE: 25
cctacttcgg taaggtttag agtcgt 26

<210> SEQ ID NO 26
<211> LENGTH: 17
<212> TYPE: DNA
<213> ORGANISM: Artificial Sequence
<220> FEATURE:
<223> OTHER INFORMATION: Description of Artificial Sequence:J123R

<400> SEQUENCE: 26
tctccgagag gcccgac 17

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence:J124R

<400> SEQUENCE: 27
aagcctggtc cagacctcca ccc 23

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence:J125R

<400> SEQUENCE: 28
aaggatcatt aatagagcaa tggatagac 29

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence:J126R

<400> SEQUENCE: 29
cgccccggga gaaatcctgg 20

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence:J127R -continued

<400> SEQUENCE: 30
tgggggccac cctacttc 18

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence:JB537

<400> SEQUENCE: 31
gggggctacc ctacttggta g 21

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence:JB541

<400> SEQUENCE: 32
ccactgattt tagaggccgc gag 23

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence:JB540

<400> SEQUENCE: 33
gggggccacc ctacttcggt aa 22

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence:JB542

<400> SEQUENCE: 34
ccactgattt tagaggccgc gaa 23

<210> SEQ ID NO 35
<211> LENGTH: 17
<212> TYPE: DNA
<213> ORGANISM: Artificial Sequence
<220> FEATURE:
<223> OTHER INFORMATION: Description of Artificial Sequence:forward sequencing primer

<400> SEQUENCE: 35
gtaaaacgac ggccagt 17

<210> SEQ ID NO 36
<211> LENGTH: 17
<212> TYPE: DNA
<213> ORGANISM: Artificial Sequence
<220> FEATURE:
<223> OTHER INFORMATION: Description of Artificial Sequence:reverse sequencing primer

<400> SEQUENCE: 36
caggaaacag ctatgac 17

-continued

<210> SEQ ID NO 37
<211> LENGTH: 627
<212> TYPE: DNA
<213> ORGANISM: Tapesia acuformis

<400> SEQUENCE: 37
tccgtaggtg aacctgcgga aggatcatta atagagcaat ggatagacag cgccccggga 60
gaaatcctgg gggccaccct acttcggtaa ggtttagagt cgtcgggcct ctcggagaag 120
cctggtccag acctccaccc ttgaataaat tacctttgtt gctttggcag ggcgcctcgc 180
gccagcggct tcggctgttg agtacctgcc agaggaccac aactcttgtt tttagtgatg 240
tctgagtact atataatagt taaaactttc aacaacggat ctcttggttc tggcatcgat 300
gaagaacgca gcgaaatgcg ataagtaatg tgaattgcag aattcagtga atcatcgaat 360
ctttgaacgc acattgcgcc ctctggtatt ccgggggca tgcctgttcg agcgtcatta 420
taaccactca agctctcgct tggtattggg gttcgcgtct tcgcggcctc taaaatcagt 480
ggcggtgcct gtcggctcta cgcgtagtaa tactcctcgc gattgagtcc ggtaggttta 540
cttgccagca acccccaatt ttttacaggt tgacctcgga tcaggtaggg atacccgctg 600
aacttaagca tatcaataag cggagga 627

<210> SEQ ID NO 38
<211> LENGTH: 626
<212> TYPE: DNA
<213> ORGANISM: Tapesia yallundae

<400> SEQUENCE: 38
tccgtaggtg aacctgcgga aggatcatta atagagcaat gaacagacag cgccccggga 60
gaaatcctgg gggctaccct acttggtagg gtttagagtc gtcaggccgc tcggagaagc 120
ctggttcaga cctccaccct tgaataaatt acctttgttg ctttggcagg gcgcctcgcg 180
ccagcggctt cggctgttga gtacctgcca gaggaccaca actcttgttt ttagtgatgt 240
ctgagtacta tataatagtt aaaactttca acaacggatc tcttggttct ggcatcgatg 300
aagaacgcag cgaaatgcga taagtaatgt gaattgcaga attcagtgaa tcatcgaatc 360
tttgaacgca cattgcgccc tctggtattc cgggggcat gcctgttcga gcgtcattat 420
aaccactcaa gctctcgctt ggtattgggg ttcgcgtcct cgcggcctct aaaatcagtg 480
gcggtgcctg tcggctctac gcgtagtaat actcctcgcg attgagtccg gtaggtttac 540
ttgccagtaa cccccaattt tttacaggtt gacctcggat caggtaggga tacccgctga 600
acttaagcat atcaataagc ggagga 626

<210> SEQ ID NO 39
<211> LENGTH: 415
<212> TYPE: DNA
<213> ORGANISM: Tapesia acuformis

<400> SEQUENCE: 39
gggggccacc ctacttcggt aaggtttaga gtcgtcgggc ctctcggaga agcctggtcc 60
agacctccac ccttgaataa attacctttg ttgctttggc agggcgcctc gcgccagcgg 120
cttcggctgt tgagtacctg ccagaggacc acaactcttg tttttagtga tgtctgagta 180
ctatataata gttaaaactt tcaacaacgg atctcttggt tctggcatcg atgaagaacg 240
cagcgaaatg cgataagtaa tgtgaattgc agaattcagt gaatcatcga atctttgaac 300
gcacattgcg ccctctggta ttccgggggg catgcctgtt cgagcgtcat tataaccact 360

-continued caagctctcg cttggtattg gggttcgcgt cttcgcgggc ctctaaaatc agtgg 415

<210> SEQ ID NO 40
<211> LENGTH: 415
<212> TYPE: DNA
<213> ORGANISM: Tapesia yallundae

<400> SEQUENCE: 40
gggggctacc cctacttggt agggtttaga gtcgtcaggc ctctcggaga agcctggttc 60
agacctccca cccttgaata aattaccttt gttgctttgg cagggcgcct cgcgccagcg 120
gcttcggctg ttgagtacct gccagaggac cacaactctt gtttttagtg atgtctgagt 180
actatataat agttaaaact ttcaacaacg gatctcttgg ttctggcatc gatgaagaac 240
gcagcgaaat gcgataagta atgtgaattg cagaattcag tgaatcatcg aatctttgaa 300
cgcacattgc gccctctggt attccggggg gcatgcctgt tcgagcgtca ttataaccac 360
tcaagctctc gcttggtatt ggggttcgcg tcctcgcggc ctctaaaatc agtgg 415

<210> SEQ ID NO 41
<211> LENGTH: 554
<212> TYPE: DNA
<213> ORGANISM: Triticum aestivum
<220> FEATURE:
<221> NAME/KEY: misc_feature
<222> LOCATION: (104)..(355)
<223> OTHER INFORMATION: cytochrome b-559 coding sequence

<400> SEQUENCE: 41
tctcacaagg aatgaaatat cagtaatttt ctatttactg gtcgatccca tcttttacgg 60
aatcaattcc tttttgaatg tacaaaaatt ttgggagttc agcatgtctg gaagcacggg 120
agaacgttct tttgctgata ttattaccag tattcgatac tgggttattc atagcattac 180
tataccttcc ctattcattg cgggttggtt atttgtcagt acgggtttag cttatgacgt 240
gtttggaagt cctaggccaa acgagtattt cacggaaagc cgacaaggaa ttccgttaat 300
aaccgaccgt tttgattctt tagaacaact cgatgaattt agtagatcct tttaggaggc 360
cctcaatgac catagatcga acctatccta tttttacagt gcgatggctg gctattcacg 420
gactagctgt acctactgtt tttttcttgg gatcaatatc agcaatgcag ttcatccaac 480
gataaaccaa attccaacta tagaactatg acacaatcaa acccgaatga acaaaatgtt 540
gaattgaatc gtag 554

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: WCP2

<400> SEQUENCE: 42
cagtgcgatg gctggctatt 20

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: WCP3

<400> SEQUENCE: 43
cgttggatga actgcattgc t 21

-continued

```
<210> SEQ ID NO 44
<211> LENGTH: 37
<212> TYPE: DNA
<213> ORGANISM: Artificial Sequence
<220> FEATURE:
<223> OTHER INFORMATION: Description of Artificial Sequence: WCP1

<400> SEQUENCE: 44

acggactagc tgtacctact gtttttttct tgggatc                            37
```